United States Patent

Kurth et al.

[11] Patent Number: 5,792,118
[45] Date of Patent: Aug. 11, 1998

[54] PERMANENT CATHETER WITH AN EXTERIOR BALLOON VALVE AND METHOD OF USING THE SAME

[76] Inventors: Paul A. Kurth, 30423 Miraleste Dr., Rancho Palos Verdes, Calif. 90274; Jon Kagan, 5112 Russell Ave. South, Minneapolis, Minn. 55410

[21] Appl. No.: 764,061

[22] Filed: Dec. 12, 1996

Related U.S. Application Data

[63] Continuation of Ser. No. 396,196, Feb. 24, 1995, abandoned, which is a continuation-in-part of Ser. No. 206,583, Mar. 7, 1994, abandoned.

[51] Int. Cl.[6] .................................................. A61M 5/00
[52] U.S. Cl. .................................. 604/246; 604/280
[58] Field of Search ........................... 604/96, 101, 246, 604/280; 606/192, 194

[56] References Cited

U.S. PATENT DOCUMENTS

| | | | |
|---|---|---|---|
| 5,178,608 | 1/1993 | Winters | 604/99 |
| 5,271,383 | 12/1993 | Wilk | 128/6 |
| 5,331,947 | 7/1994 | Shturman | 128/4 |
| 5,403,274 | 4/1995 | Cannon | 604/9 |
| 5,437,638 | 8/1995 | Bowman | 604/101 |

*Primary Examiner*—Corrine M. McDermott
*Attorney, Agent, or Firm*—Daniel L. Dawes

[57] ABSTRACT

An permanent indwelling catheter is provided with a selectively inflatable exterior balloon valve to to seal one or more orifices defined in the catheter wall or tip. The longitudinal lumen may either comprise a single central axial lumen or a plurality of subdivided lumens within the catheter body. The orifices may be defined through the side wall of the catheter at variable points along its length and/or may be defined in the tip of the catheter. In embodiment, the expansible membrane is disposed in the proximity of a distal tip orifice and is inflated to completely fill the space of the tip and extend into the tip orifice to seal it. In yet another embodiment, the membrane valve, is comprised of two or more separate membrane portions which are simultaneously inflated against each other and adjacent surfaces within the catheter to provide a sealing wall and means for sealing the orifice.

18 Claims, 8 Drawing Sheets

PERMANENT CATHETER WITH AN EXTERIOR BALLOON VALVE AND METHOD OF USING THE SAME

RELATED APPLICATIONS

This is a continuation of application Ser. No. 08/396,196 filed on Feb. 24, 1995, now abandoned, which is a continuation in part of a copending application, Ser. No. 08/206,583, filed Mar. 7, 1994, now abandoned.

BACKGROUND OF THE INVENTION

1. Field of the Invention

The field of the invention relates to permacaths or permanent catheters, that is catheters, which are most often used in dialysis, chemotherapy, antibiotic and nutritional therapy, and which are placed in veins or arteries for long periods of time such as several days to even years during which time substances are controllably dispensed through the catheter into the patient's circulatory system and wherein blood is continuously or intermittently withdrawn or processed, and returned or replaced.

2. Description of the Prior Art

The conventional procedure is after use of the permacath is to flush it with Heparin, a well-known anticlotting agent. The purpose of filling the catheter with Heparin is to prevent blood clotting within the catheter. However, notwithstanding these precautions, clotting does occur and urakinase, a blood clot solvent, often must be used to clear the catheter. The process is time consuming, potentially dangerous to the patient, sometimes difficult and requires the services of a skilled nurse or doctor.

Catheters having various means for closing about a guide wire disposed in the catheter lumen are known. Hohn, "*Valved Arterial Catheter,*" U.S. Pat. No. 5,147,318 (1992) shows a catheter used for permanent or extended insertion in an artery. The distal end of the catheter 10 shaft is provided with a valve 16. Valve 16 is defined by a slit 30 formed in a hemispherical surface of silicone rubber from which the valve body is formed. The tip is designed so that it will open under relatively low pressures, yet will self-seal completely to prevent blood from backflowing through the valve. The thickness of the silicone rubber at the hemispherical tip end and the region of the slit is such that the slit valve will open at pressures of less than about 10 psi injection pressure, typically 3 to 4 psi. The valve will maintain flow rates on the order of 4 milliliters per minute at a pressure of about 10 psi.

Winters, "*Balloon Catheter with Expandable Inflation Member,*" U.S. Pat. No. 5,178,608 (1993) shows a catheter including balloon valves to expand into coaxial lumens. Winters is characterized as a single lumen catheter wherein the single lumen can be occluded by a special balloon guidewire 62. Winters teaches using small inflatable collars to trap a catheter and not to close a noncoaxial central lumen without any other occluding element or guide wire present.

Burns et al., "*Innerless Dilatation Balloon Catheter,*" U.S. Pat. No. 5,221,260 (1993), describes a balloon catheter which is designed to trap a guidewire inside a catheter for improved pressability. Catheter shaft 10 includes a pressure responsive valve 25 which is shown in the nonextended position in FIG. 1 and in the extended position in FIG. 2. Fluid flow through lumen 16 is controlled by means of valve 25 which is responsive to pressure provided in the interior of balloon 11. Pressure causes valve 25 to converge to guide wire 12 and trap it.

Horzewski et al., "*Vascular Catheter with Releasably Secured Guidewire,*" U.S. Pat. No. 4,932,959 (1990) shows a catheter having a flexible inflatable section best depicted in FIGS. 2 and 3. In FIG. 3, an inner tubular element 21 with flexible section 23 defines an inflation chamber 24. Fluid under pressure from annular passageway 22 fills inflation chamber 24, causing flexible section 23 to expand inwardly to engage and trap guide wire 16. Again, Horzewski shows an inflatable valve for trapping a guide wire in a catheter.

Arney, "*Innerless Dilatation Catheter with Balloon Stretch Valve,*" U.S. Pat. No. 5,217,434 (1993) shows another design for a valve and a catheter for trapping a guide wire. As best depicted in FIG. 2, elongation of balloon 22 due to inflation causes valve 30 to stretch. As valve 30 is stretched, an intermediate section 70 increases and the inner diameter of section 70 correspondingly decreases. Valve 30 thus decreases the inner diameter of the lumen extension to trap a guidewire for greater pressability across a stenous. Again, a guide wire is being trapped.

Davis, Jr., "*Indwelling Urethral Catheter,*" U.S. Pat. No. 4,432,757 (1984) shows an indwelling or permanent catheter having a valve 32. In FIGS. 4a and 4b, operation of the valve 32 is shown as being urged against a seat 26 by plastic spring clips 38 which are normally biased to the closed position. The valve is selectively opened by the patient to drain the urethra.

Erlich, "*Catheter with Check Valve and Rolled Sheath,*" U.S. Pat. No. 5,181,913 (1993) shows a catheter with a check valve in FIG. 1a for limiting flow in a single direction. A one-way valve 25 designed with two or more flaps 27 and 28 which allow fluid to pass only in one direction.

What is needed is some kind of a design for a balloon valve which is capable of fully occluding and sealing off one or more lumens in a permanent catheter and thereby prevent blood from clotting off the inner lumen.

BRIEF SUMMARY OF THE INVENTION

The invention is a permanent catheter comprising a catheter body defining a lumen within the body. A membrane valve is disposed exterior to the lumen. At least one orifice is defined in the catheter body through which fluid within the lumen may communicate exteriorly to the catheter body. The membrane valve is inflatable to at least partially to obstruct flow therethrough. As a result, the permanent catheter is subject to minimal risk of occlusion by bodily fluids.

In the preferred embodiment orifice is a tip orifice of the catheter although side wall orifices are contemplated as being exteriorly sealed as well. In the preferred embodiment the membrane valve substantially seals the orifice, but all that is required under the invention as conceived is obstruction of the orifice coupled with a minimal pressure gradient thereacross.

The membrane valve is has an uninflated and inflated configuration and is disposed in the uninflated configuration entirely exterior to the lumen so that flow obstruction and clot formation in the lumen due to the membrane valve even when uninflated is substantially avoided.

The catheter further comprises a moveable valve flap and the membrane valve comprises an inflatable balloon and the flap actuated by the balloon to substantially seal the orifice. In another embodiment the catheter further comprises a guide and the membrane valve then comprises an inflatable balloon whose inflation is guided by the guide to substantially seal the orifice.

In general the catheter body further comprises a septum wall. The septum wall divides the catheter body into a plurality of longitudinal lumens. The orifices are defined in the catheter body to communicate each of the longitudinal lumens exterior to the catheter body. The catheter further comprises a corresponding plurality of membrane valves disposed on the septum wall. Each of the plurality of membrane valves is disposed exterior to the corresponding one of the orifices. The septum wall may be excluded by appropriate catheter design.

At least two of the plurality of the membrane valves are serially inflated. Alternatively, at least two of the plurality of the membrane valves are inflated in parallel.

The lumen is free of all other occluding elements which might impede flow of fluid therethrough other than the membrane valve. The lumen is closed solely by the membrane valve without coaction with any other element within the lumen.

In one embodiment the orifice is a tip orifice and the valve membrane is affixed to the catheter adjacent to the orifice and is formed to inflate in the shape of at least a portion of a tear drop having a blunt end disposed toward tip orifice. The blunt end of the valve membrane has a peripheral edge which is folded under and bonded to the catheter.

In another embodiment the orifice is a tip orifice, the valve membrane is affixed to the catheter adjacent to the orifice and is formed to inflate in the shape of at least a portion of an oval having a narrowed end disposed toward tip orifice. The oval shaped valve membrane is not folded under along its peripheral edges where it is bonded to the catheter.

In still yet another embodiment the orifice is a tip orifice, the valve membrane is affixed to the catheter adjacent to the orifice, and is formed to inflate in the shape of at least a portion of a sphere.

The invention is also characterized as a method for selectively sealing a lumen defined within a catheter comprising the steps of providing an expansible membrane on an extending wall adjacent but exterior to an orifice of the lumen. The expansible membrane is selectively expanded to substantially seal the orifice. As a result, the catheter may be used as a permanent indwelling catheter.

A single membrane is provided, and selectively sealing the orifice further comprises unfolding the single membrane to substantially seal the orifice.

In the case where a plurality of expansible membranes are provided, they are coupled together in series so as to be simultaneously inflatable. One of the expansible membranes selectively occludes the lumen and the other one of the inflatable membranes seals the orifice.

The invention may be better visualized by now turning to the following drawings wherein like elements are referenced by like numerals.

BRIEF DESCRIPTION OF THE DRAWINGS

FIG. 17b is a top plan view of the portion illustrated in FIG. 17a.

FIG. 18b is a top plan view of the portion illustrated in FIG. 18a.

The invention and its various embodiments may be better understood by now turning to the following detailed description.

DETAILED DESCRIPTION OF THE PREFERRED EMBODIMENTS

An permanent indwelling catheter is provided with a selectively inflatable exterior balloon valve to to seal one or more orifices defined in the catheter wall or tip. The longitudinal lumen may either comprise a single central axial lumen or a plurality of subdivided lumens within the catheter body. The orifices may be defined through the side wall of the catheter at variable points along its length and/or may be defined in the tip of the catheter. In embodiment, the expansible membrane is disposed in the proximity of a distal tip orifice and is inflated to completely fill the space of the tip and extend into the tip orifice to seal it. In yet another embodiment, the membrane valve, is comprised of two or more separate membrane portions which are simultaneously inflated against each other and adjacent surfaces within the catheter to provide a sealing wall and means for sealing the orifice.

Figure 1:
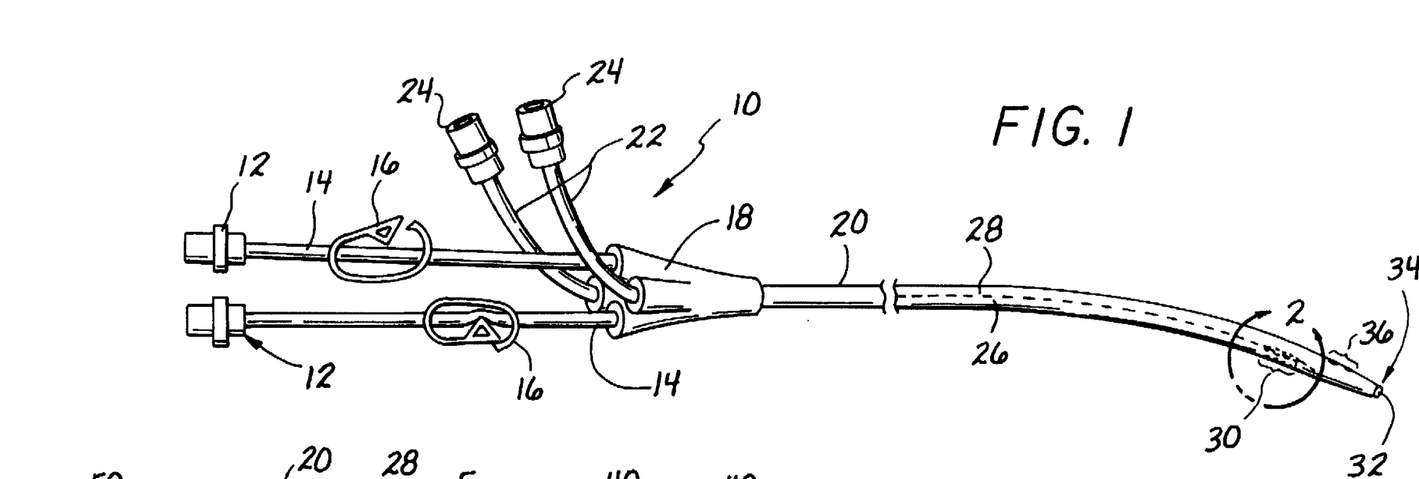
FIG. 1 is a perspective view of a permanent catheter shown in partially cutaway view.

Before considering the exterior balloon, consider first the embodiments where interior balloon valves are employed. FIG. 1 is a partially cutaway side view of a profusion or permanent catheter, generally denoted by reference numeral 10, which has been modified to include a pair of inflatable balloon valves according to the invention. Catheter 10 is provided with a pair of conventional fittings 12 through which fluid may be injected or ejected from catheter 10. Fittings 12 may include conventional hemostatic valve or other means known to the art for controlling flow fluids into or out of catheter 10. The details and mechanism which may be included within fittings 12 is not material to the invention and, therefore, will not be further described in detail nor should be considered limiting.

Fittings 12 are coupled to the corresponding tubes 14 each of which may be provided with conventional tubal compression valve 16, one of which is shown in an open configuration in side view in FIG. 1 and the other one of which is shown in side view in a closed configuration. Compression valves 16 are manually activated and are conventionally used to pinch off flexible tubing 14 to prevent flow in either direction according to the procedure which may be used at the time.

Tubes 14 are combined in a conventional Y connector 18 which communicates each of tubes 14 to a separate lumen within catheter body 20. Many different configurations and designs may be used for Y connector 18 other than that depicted in FIG. 1. Again, the details of connector 18 are largely immaterial to the invention and the essence is that tubes 14 are by some means now known or later devised communicated with separate lumens or tubes within catheter body 20 as will be described in the following figures.

In addition to the lumens coupled to tubes 14, in the illustrated embodiment of FIG. 1, two additional tubes or lumens within catheter body 20 are also communicated to inflation tubes 22 and their respective end fittings 24. These tubes and fittings allow the selective insertion of a fluid or gas to inflate the balloons within catheter body 20 to selectively close off either one of the two major lumens within catheter body 20 or the inlet and outlet orifices. For example in the illustration of FIG. 1, catheter body 20 includes a first primary lumen 26 and a second primary lumen 28 communicated with tubes 14 through connector 18. Lumen 26 in turn is provided with a plurality of ports 30, which in this case, may be inlet ports allowing blood to be drawn in through ports 30 into lumen 26 for processing in extrinsic apparatus, such as a dialysis machine or the like. The second primary lumen 28 is communicated with an outlet orifice 32 at tip 34 of catheter body 20 and with a plurality of auxiliary outlet ports 36 in vicinity of tip 34. The number and positioning of orifices 30, 32 and 36 is largely immaterial to the invention as is the specific topology within catheter body 20. One example is shown in FIG. 1 only for purposes of illustration.

Figure 2:
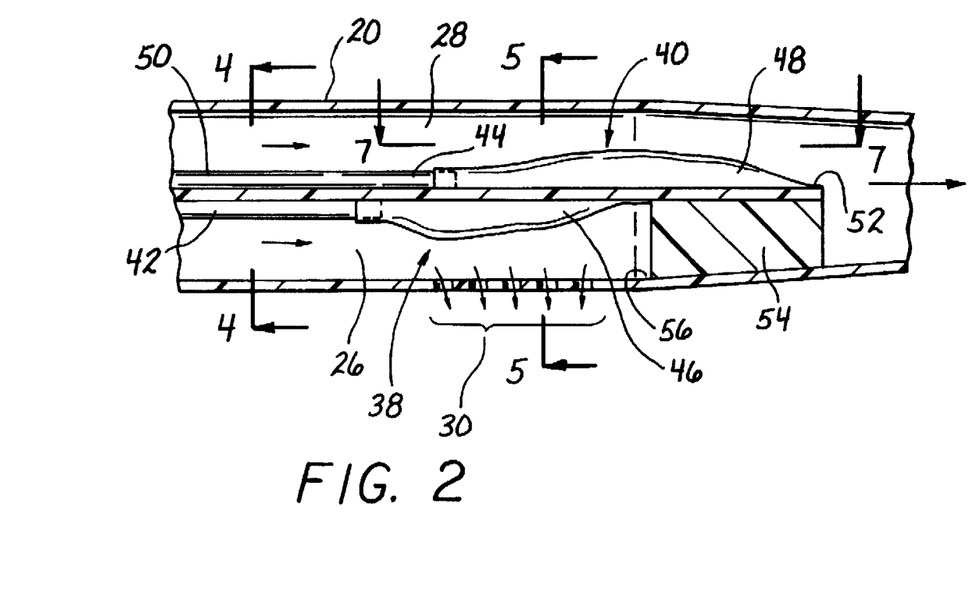
FIG. 2 is a diagrammatic side cross-sectional view in enlarged scale of that portion of the catheter in FIG. 1 included within insert lines 2—2.

Turn to FIG. 2 which is an enlarged cross-sectional view of that portion of catheter body 20 within circle 2—2 of FIG. 1. Each primary lumen 26 and 28 is provided with a balloon valve, generally denoted by reference numerals 38 and 40, respectively. In the illustrated embodiment, balloon valves 38 and 40 are comprised of a delivery tube 42 and 44, respectively, disposed in corresponding lumens 26 and 28. Delivery tubes 42 and 44 in turn communicate with a folded expansible balloon membrane 46 and 48, respectively.

In the illustrated embodiment, primary lumen 26 ends upstream from tip 34, the two lumen walls being separated by a septum 50 which may be extrusion molded as part of catheter body 20. Septum 50 may be reinforced and sealed at its distal end 52 by means of a tapered plug 54 bonded between septum 50 and the inside wall 56 of catheter body 20 within lumen 26. Again the means or construction by which separate lumens are formed within catheter body are illustrative only.

Figures 3, 5, 6, 7:
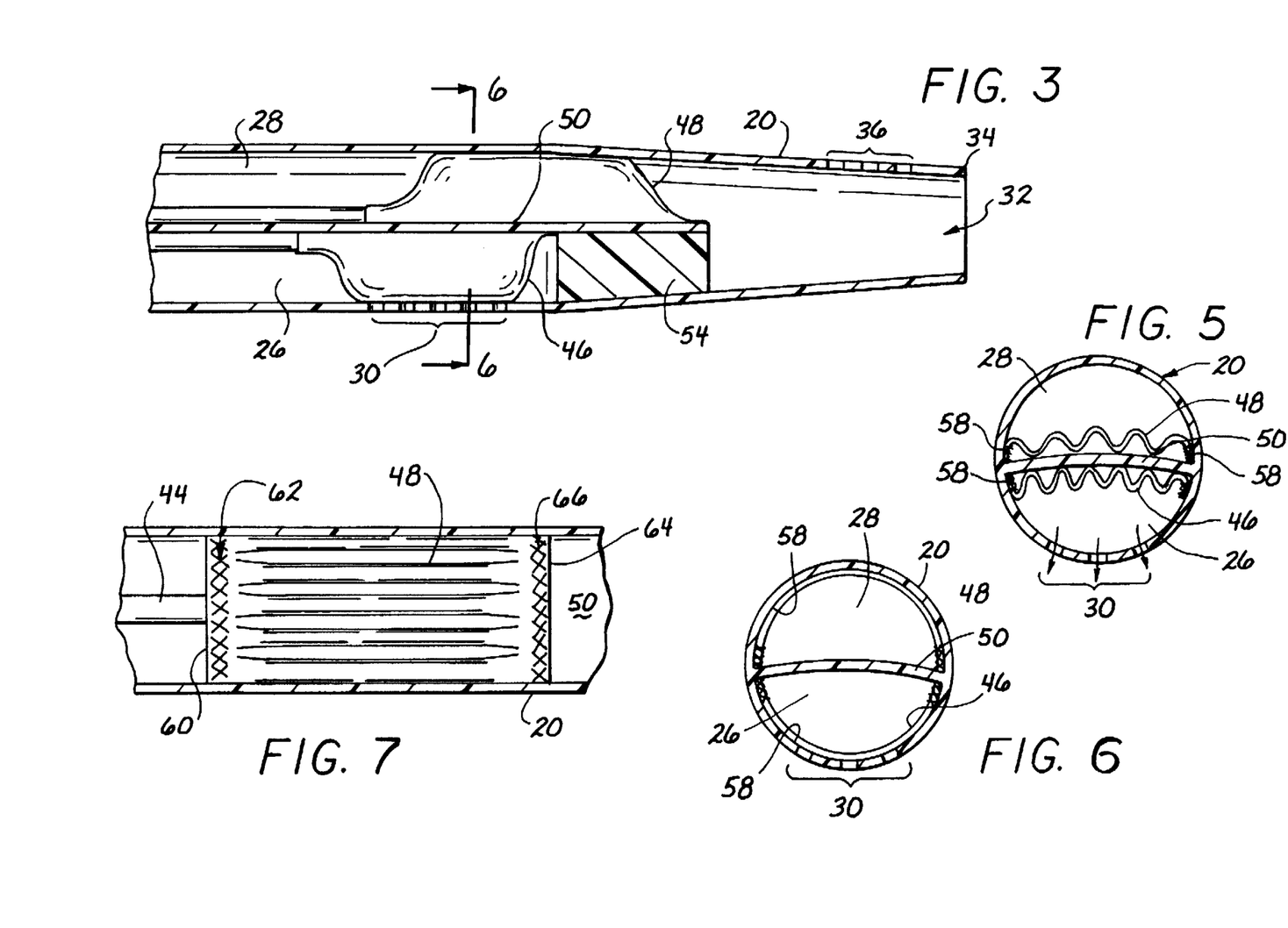
FIG. 3 is a diagrammatic side cross-sectional view of catheter of FIG. 2 after the balloon valves have been inflated.
FIG. 5 is a diagrammatic perpendicular cross-sectional view of the catheter tip of FIG. 2 as seen through section lines 5—5 of FIG. 2.
FIG. 6 is a diagrammatic perpendicular cross-sectional view of the catheter tip of FIG. 3 showing the balloon valve after inflation as seen through section lines 6—6 of FIG. 3.
FIG. 7 is a top plan view in enlarged scale of the catheter tip of FIG. 1 as seen through section lines 7—7 of FIG. 2.

The simplified side cross-sectional view of FIG. 3 shows the catheter tip after the balloon valves have been inflated. The embodiment of FIG. 3 is shown only for purposes of illustration to indicate that a balloon closable valve of the invention can either be used to directly close the orifices in the catheter, such as orifices 30 in primary lumen 26, or can be used to effectively block the entire lumen at any point upstream from its corresponding orifices as shown in the case of lumen 28. In an actual application, it may be interest to entirely block the interior of any and all of the lumens within catheter body 20, rather than to leave a tip portion still in communication with bodily fluids such as suggested in FIG. 3. The alternative embodiment illustrated in FIGS. 8 and 9 and discussed below shows one example in which the entire interior of a catheter may be selectively closed. In the extreme limiting case, the entire length of the catheter may be provided with a running membrane which may occlude and close the entire catheter lumen.

Figure 4:
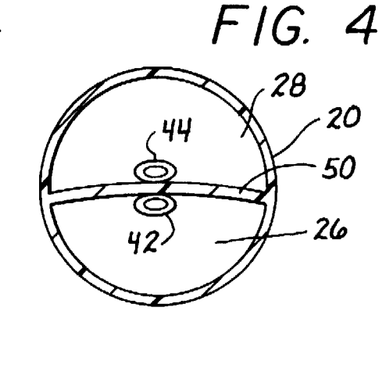
FIG. 4 is a diagrammatic perpendicular cross-sectional view of the catheter tip of FIG. 2 as seen through section lines 4—4 of FIG. 2.

The operation of catheter shown in FIG. 2 is better understood by viewing the cross-sectional depictions taken through lines 4—4 and 5—5 of FIG. 2. In the illustrated embodiment, FIG. 4 shows catheter body 20 with the extrusion molded septum 50 at a position proximal from balloon valves 38 and 40. The separate primary lumens 26 and 28 are clearly shown in the disposition with each of them of their corresponding inflation tubes 42 and 44 as depicted. Tubes 42 and 44 may be adhered to or otherwise bonded to septum 50 to provide a means by which small amounts of fluid and pressure needed to inflate balloon valves 38 and 40 are provided. Alternatively, tubes 42 and 44 may be fabricated integrally into the catheter wall or into one or more septums defined within the catheter.

FIG. 5 is an enlarged cross-sectional view taken through section lines 5—5 of FIG. 2 showing folded balloons 46 and 48 within lumens 26 and 28 respectively. Balloons 46 and 48 are affixed, bonded and otherwise adhered to inner wall 58 across a portion of their contact symbolically denoted in FIG. 5 by a series of X's. The thin extensible material of each membrane comprising balloons 46 and 48 is laid against inner wall 58 of catheter body 20 leading in a direction in which balloons 46 and 48 will expand. For example, the cross section of FIG. 5 which shows balloon 46 and 48 folded across septum 50 are shown in inflated cross-sectional view in FIG. 6. The membranes comprising balloons 46 and 48 have expanded to conform to inner wall 58 of catheter body 20 thereby completely closing off lumen 28 upstream of its orifices 36 and 32 and directly closing off orifice 30 defined in primary lumen 26.

Returning your attention to the embodiment of FIGS. 1 and 2, a top plan cross-sectional view of balloon valve 40 is seen through sectional lines 7—7 of FIG. 2 is depicted in FIG. 7. Membrane 48 is diagrammatically depicted as being an accordion-folded rectangular membrane, which is bonded on its periphery to septum wall 50 and/or interior surfaces 58 of catheter body 20. Inflation tube 44 is disposed under one end 60 of membrane 48 which has been sealed thermally or adhesively across septum wall 50 and over tube 44 in region 62. The opposing end edge 64 of membrane 48 is similarly sealed by affixation or bonding in region 66 to septum wall 50. Sealing region 62 and 66 together with sealing regions 58 as shown in FIG. 5 thereby completely seal and close the periphery of accordion-folded membrane 48 allowing it to form a fluid or air tight space between membrane 48 and at least septum wall 50.

Membrane 48 or 46 may then be inflated by its respective inflation tubes 44 and 42, respectively, through the injection of fluid or air through a hypodermic needle through fixtures 24 and tubes 22 to form the expanded in orifice sealing configurations depicted in FIG. 6. Although the illustrated embodiment has shown the membranes 46 and 48 as being accordion folded or pleated, the manner of folding, pleating, or whether it is folded at all is entirely a matter of design choice. It is also within the contemplation of the invention that membranes 46 and 48 may be comprised of material which is inherently resilient and expandable without the need for folding.

Figures 8, 9:
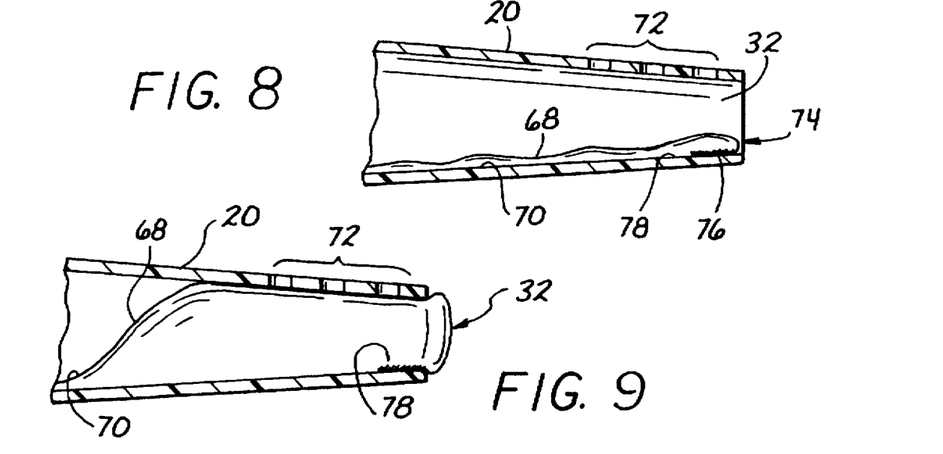
FIG. 8 is a diagrammatic side cross-sectional view of the catheter tip of another embodiment of the invention.
FIG. 9 is a diagrammatic side cross-sectional view of the catheter tip of FIG. 8 after the valve has been inflated and the catheter tip occluded.

FIGS. 8 and 9 represent another embodiment of the invention in which a membrane 68 may, for example, be bonded or integrally formed with a control tube or lumen 70 and configured so as to unroll when it expands to close catheter orifices 72. For example, in the embodiment of FIG. 8, membrane 68 forms a generally single folded loop 74 which is attached to catheter body 20 at a region 76. The remainder of membrane 68 is free to unroll or expand from inner wall 78 of catheter body 20.

Therefore, as membrane 68 is inflated, as shown in the cross-sectional enlarged view of FIG. 9 of the tip of catheter 10, it expands across the diameter of the catheter tip not only to seal side wall orifices 72, but also to make a fluid tight seal in tip 32 forming over the lip of tip orifice 32 somewhat like a loaf of bread spilling over the lip of a loaf pan to form a complete circumferential seal about tip orifice 32 as well.

Figure 10:
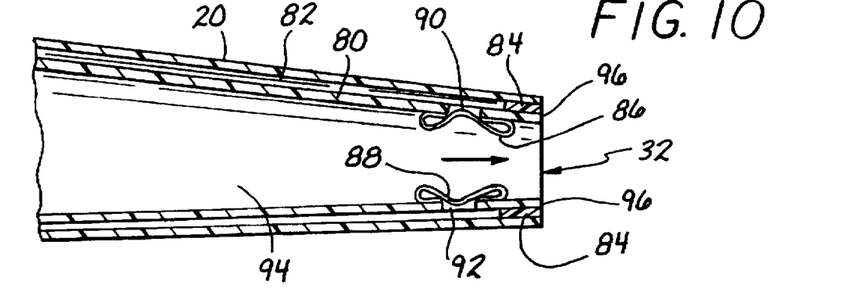
FIG. 10 is a diagrammatic side cross-sectional view of another embodiment of the catheter tip.
Figure 11:
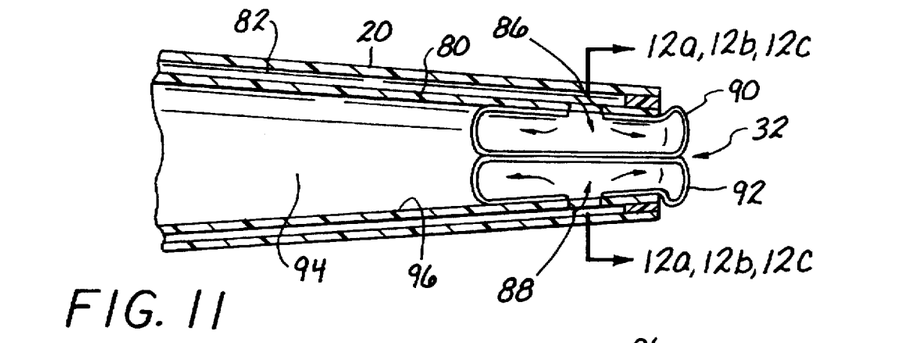
FIG. 11 is a diagrammatic side cross-sectional view of the catheter tip of FIG. 10 after the valve has been inflated.

FIGS. 10 and 11 are enlarged side cross-sectional views of an orifice tip of catheter 10 showing another embodiment of the invention. In the embodiment of FIG. 10, the catheter is, for example, comprised of an outer body wall 20 and an inner body wall 80 defining a lumen 82 between them. The structure is in effect one catheter disposed inside of another larger one. The concentric tubes 20 and 80 are sealed at their end by means of a ring plug 84. Upstream from ring plug 84 are two or more annular orifices 86 and 88.

The embodiment of FIGS. 10–12c are distinguished from the other embodiments of the invention in that no inflation tubes similar to tubes 42 or 44 are used, but the concentric space defined between concentric catheters of different diameters is used as the inflation channel. The two catheters 20 and 80 are rigidly fixed with respect to each other by means of end ring plug 84, which also supports the portion of catheter 80 which is connected to membranes 90 and 92 in FIG. 12a, membrane 93 in FIG. 12b and membranes 97 in FIG. 12c. The opposing or proximal ends of catheters 20 and 80 are connected to fitting 18 similar to that shown in FIG. 1 which provides separate fluidic access to lumens 82 and 94 through a conventional Y-to-concentric design.

In a first embodiment two valve membranes are provided. Thus, sealed across and spanning each orifice is a corresponding extensible membrane 90 and 92, respectively. Membranes 90 and 92 may be folded one or more times across their respective orifices 86 and 88 to provide sufficient material to add to the inherent resiliency to allow expansible enclosure of tip orifice 32.

FIG. 11 is a cross-sectional view of the embodiment of FIG. 10 after fluid has been injected into lumen 82 to expand membranes 90 and 92. Membranes 90 and 92 expand to a sufficient extent to completely close off tip orifice 32 and interior lumen 94 of the catheter and also expand out to the tip orifice 32 to billow over edges 96 of orifice 32 to completely fill tip orifice 32 thereby preventing the coagulation or other solidification of body fluids within tip orifice 32.

Figure 12A:
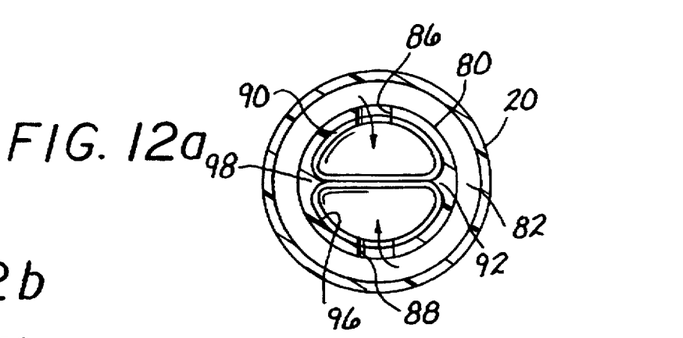
FIGS. 12a–c are diagrammatic perpendicular cross-sectional views of the catheter tip as seen through lines 12—12 of FIG. 11.

As seen in the perpendicular cross-sectional view of FIG. 12a taken through section lines 12—12 of FIG. 11, membranes 90 and 92 are inflated to contact each other to form a membrane-to-membrane contacting seal approximately in the middle of central lumen 94. The interior walls 96 of inner tube 80 may be contoured, such as through extrusion molding, to conform to the contacting surfaces of membranes 90 and 92. For example, in the perpendicular cross-sectional view of FIG. 12a, inner tube 80 has its interior walls 96 contoured to form two cusp portions 98 to conform to the membrane curvatures where the two membranes meet and thereby avoiding any sharp or right angles where adequate membrane sealing may otherwise be difficult or impractical to achieve.

Figure 12B:
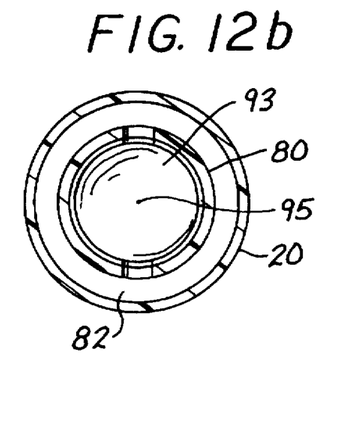

In a second embodiment of FIGS. 10 and 11 the two membranes can be replaced by a single circumferential membrane. In this case reference numerals 90 and 92 would be understood a referring to opposite sides of the same membrane valve. The closed valve is then comprised of a single integral membrane, referenced as membrance 93 in FIG. 12b, which would has the closed configuration as seen in FIG. 12b, which is termed a "holeless donut". The sectional view of FIG. 12b shows a the inside view of membrane 93 where it meets itself and seals at center 95 of the holeless donut.

Figure 12C:
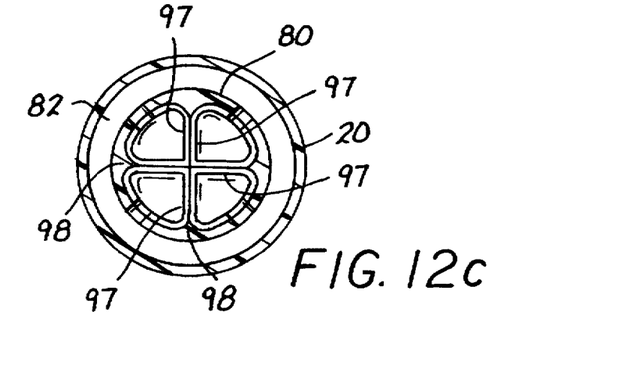

In a third embodiment of FIGS. 10 and 11 the membrane valve could be comprised of a plurality of sectors of three or more separated membranes 97 as seen in FIG. 12c. In this case closed valve would then have the closed configuration with the possible inclusions of cusp portions 98 between each sector. In the case where the material of the membrane is pliable enough a satisfactory seal might be obtained with the use of cusp portions 98.

It must be understood that the specific structures of the balloon closures can be widely varied according to the spirit of the invention. For example, a third balloon can be coupled in series with balloon valve 48 in the embodiment of FIG. 3 to provide a tip occlusion and closure in the manner as depicted in either of the embodiments of FIGS. 8 and 9 or 10–12. Therefore, the catheter of the invention may include not only side wall orifice sealing, but also tip occlusion and tip sealing either by a single membrane or by a plurality of membranes sealing the central lumen of the catheter through a membrane-to-membrane contact seal.

Figure 13:
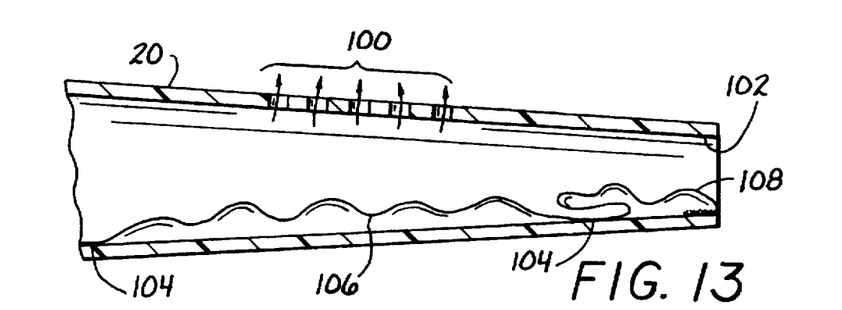
FIG. 13 is a simplified side cross sectional view of another embodiment of the invention utilizing a series of balloon valves shown in uninflated configuration.

The side or longitudinal cross sectional view of FIG. 13 shows catheter 20 having a plurality of side ports 100 defined therethrough in an orifice tip 102. Inflation tube 104 is provide to a first balloon 106. Inflation tube 104 continues or serially extends from first inflation balloon 106 to a second balloon valve 108. The view of FIG. 13 shows balloon valves 106 and 108 in an uninflated configuration. When pressure is provided through tube 104, both balloons 106 and 108 will inflate to the configuration shown in FIG. 14. Inflated balloon 106 expands across lumen 110 to completely close side ports 100. Simultaneously, pressure is provided through the extension of supply tube 104 to the end balloon valve 108 which expands to entirely close off orifice tip 102. Therefore, FIGS. 13 and 14 illustrate the situation where two or more balloon may be cascaded in series and simultaneously inflated to occlude and/or close different orifices or ports within catheter 20 within a single lumen 110.

Figure 15:
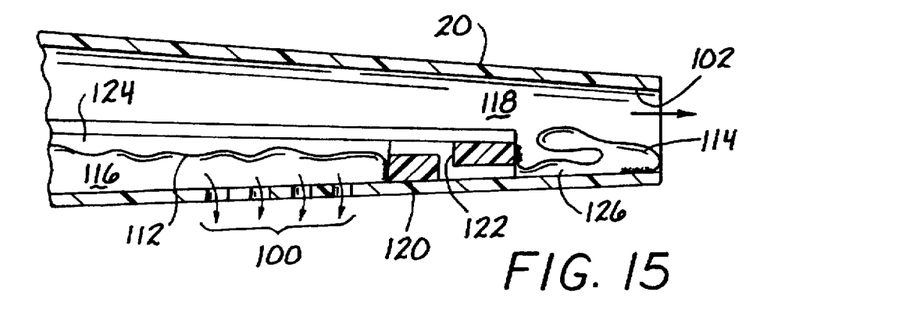
FIG. 15 is a diagrammatic side view of a catheter where the serially connected balloon valves are disposed and inflated in separate lumens.

The embodiment of FIG. 15 shows the series coupling of two or more balloon valves 112 and 114 in two separate lumens 114 and 116 of catheter 20. An inflation tube or sublumen 124 is used to inflate valve 112 which in turn is used to seal sidewall orifices 100. Tube 124 continues from valve 112 to communicate with or extend through a duct 122 defined in block 120 which seals and forms the end wall of lumen 116. An inflation tube 126 in series circuit with tube 124 and valve 112 continues along the inner wall of catheter 20 to inflate second valve membrane 114. Membrane 114 is inflated to seal tip orifice 102 and occlude the tip portion of lumen 118. Therefore, FIG. 15 illustrates the situation where two or more balloon may be cascaded in series and simultaneously inflated to occlude and/or close different orifices or ports within catheter 20 within different or uncommunicated lumens 116 and 118.

Figure 14:
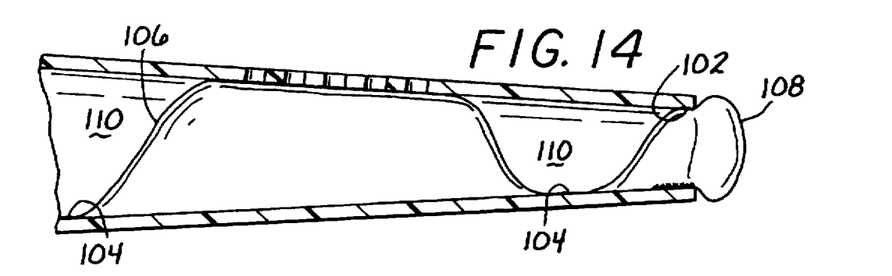
FIG. 14 is a diagrammatic side view of the catheter of FIG. 13 shown with the serially connected balloon valves disposed and inflated in the same lumen.

In addition to the series circuit of balloon valves as shown in FIGS. 13 and 14 is must be understood that the invention expressly contemplates a situation where parallel circuits may also be employed. It is expressly within the scope of the claims that any combination of series and parallel inflation circuits and their corresponding balloon valves may be employed.

Figure 16A:
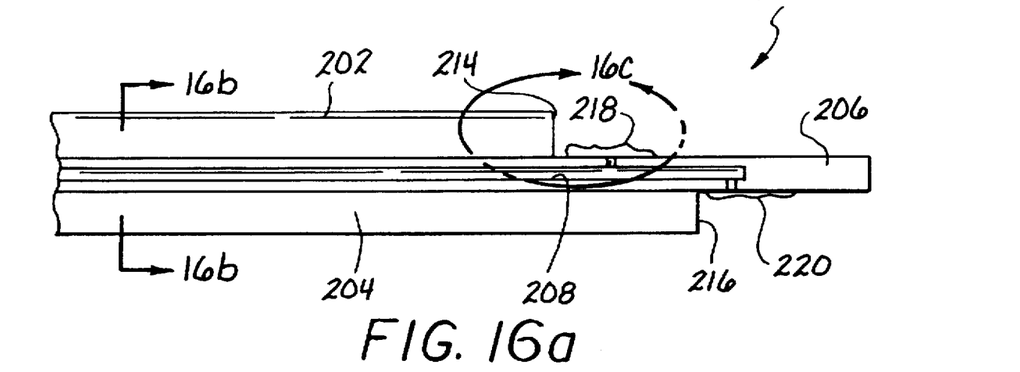
FIG. 16a is a side view of an embodiment using an exterior balloon valve.

FIG. 16a is a side elevational view of another embodiment of the invention in which catheter 200 is comprised of a first segment 202 and a second segment 204 connected to a dividing septum wall 206. Septum wall 206 has a thickness sufficient to allow one or more lumens 208 to be defined therethrough as best seen in the transverse cross sectional view of FIG. 16b taken through section lines 16b—16b of FIG. 16a.

A first principal lumen 210 is defined above septum 206 and a second principal lumen 212 defined therebelow. Lumen 210 terminates at the right end of catheter 200 as seen in FIG. 16a in a tip orifice 214. Lumen 212 similarly terminates in a tip orifice 216. Septum wall 206 extends beyond tip 214 and 216 to provide a mounting surface for an exterior balloon, namely exterior balloon 218 associated with orifice tip 214 and exterior balloon 220 associated with orifice tip 216. Balloons 218 and 220 are shown in the substantially deflated condition in FIG. 16a and, therefore, provide little, if any, flow impedance to orifice tips 214 and 216 thereby minimizing the opportunity for clotting or flow obstruction.

It is, of course, expressly understood that the embodiment of FIG. 16a may also be made with a single lumen by deletion of a lower portion 204 or may be multiplied to three or more lumens. Further the surface to which balloons 218 and 220 are attached may be provided elsewhere on catheter 200, including the exterior walls of segments 202 or 204 or in additional specially provided surfaces, such as a transverse wall (not shown) to septum wall 206.

Figure 16B:
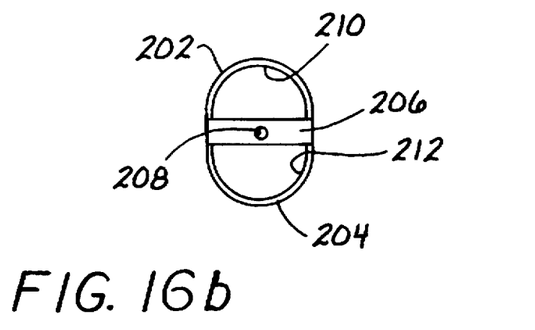
FIG. 16b is transverse cross-sectional view of the catheter of FIG. 16a as seen through section lines 16b—16b.
Figure 16C:
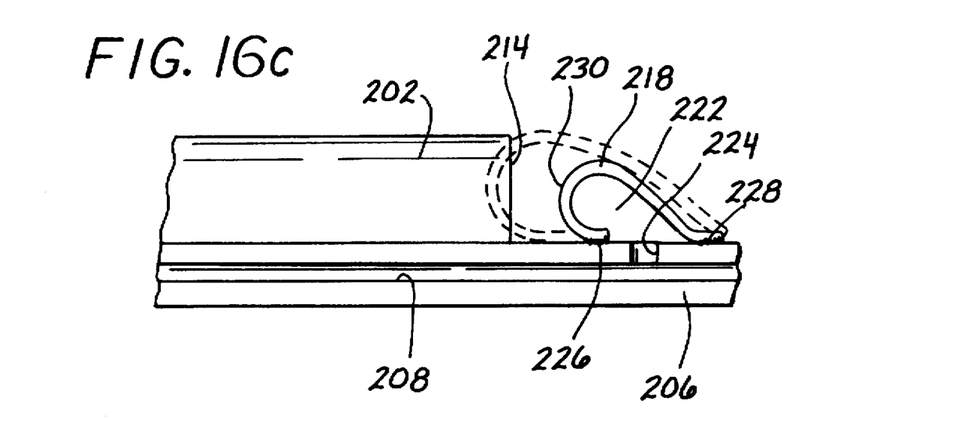
FIG. 16c is side elevational view in enlarged scale of the circled portion 16c—16c of FIG. 16a after the balloon has been inflated and sealed the lumen.

The details of operation of balloons 218 and 220 may be better understood in connection with the depiction shown in FIG. 16c which is a side elevational depiction in enlarged scale of that portion of catheter 200 shown in circle 16c—16c of FIG. 16a. The description will be made in connection only with the upper balloon 218 and orifice tip 214, although a similar description could be provided with respect to lower balloon 220 and corresponding orifice tip 216. Balloon 218 is inflated by providing air or a fluid through lumen 208 defined within septum wall 206. Lumen 208 is communicated with interior 222 of balloon 218 through an access port 224 defined through septum wall 206 into lumen 208. Lumen 208 continues forwardly within wall 206 to be similarly communicated to balloon 220. Balloons 218 and 220 are thus communicated in parallel in this embodiment. Each balloon 218 and 220 may also be provided with separate lumens for inflation like lumen 208 or serially communicated by two lumens that communicate with each other only through one of the balloons.

A proximal edge 226 of balloon 218 is folded under and away from orifice tip 214 as shown in FIG. 16c, i.e. its exterior surface is turned over and is in contact with wall 206. The opposing distal edge 228 of balloon 218 is folded flatly and also disposed away from orifice 214, i.e. its interior surface is not turned over and is in contact with wall 206. Therefore, as balloon 218 is inflated and expands, proximal surface 230 moves toward and into orifice tip 214 in a natural, unimpeded way by in essence rolling over affixed edge 226 to assume the shape as shown in dotted outline in FIG. 16c.

Figure 16D:
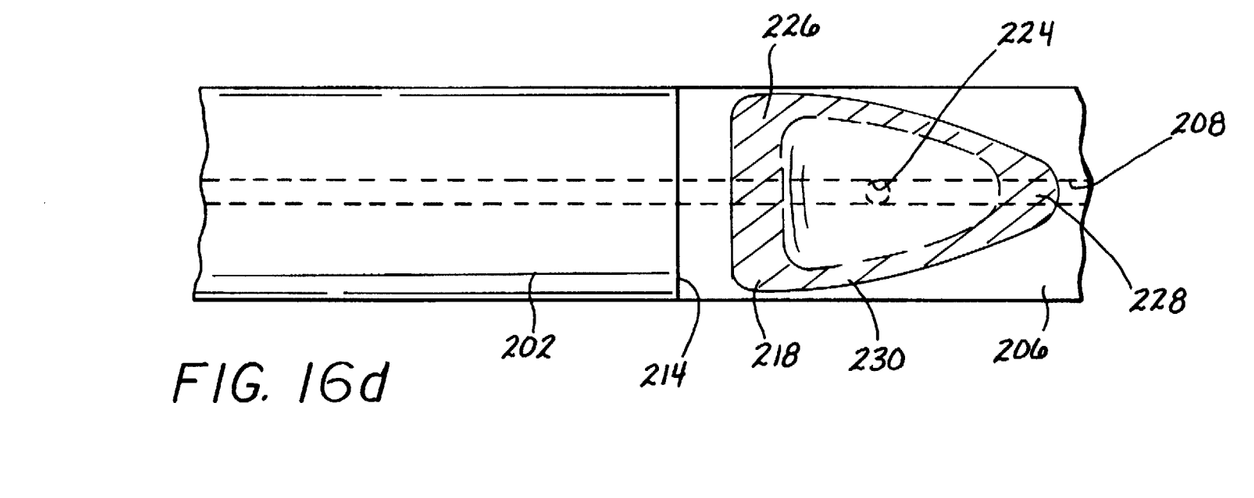
FIG. 16d is a top plan view of the portion illustrated in FIG. 16c.

The top plan view FIG. 16d illustrates the features of FIG. 16c from a top perspective and shows balloon 218 having a proximal end 226 sealed over an enlarged area with peripheral bonded seals 230 extending from proximal bonded edge 226 to distal bonded edge 228.

Figure 16E:
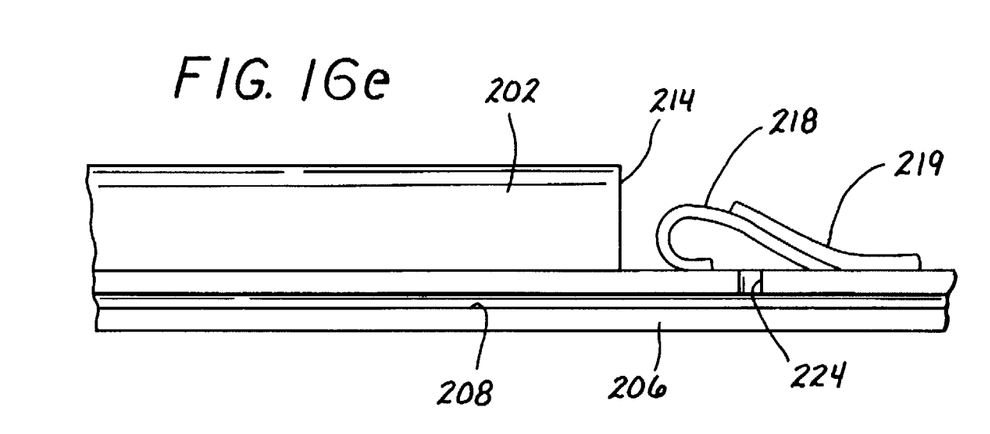
FIG. 16e is yet another embodiment of the balloon valve of FIGS. 16a–d.

As shown in FIG. 16e it is also expressly contemplated that various guides 219 could be used to assist in directing or shaping balloon 218 as it inflates to appropriately direct it to and into orifice 214 for proper seating and sealing. Guide 219 is placed on wall 206 so as to minimize flow obstruction when balloon 218 is not inflated.

Figure 17A:
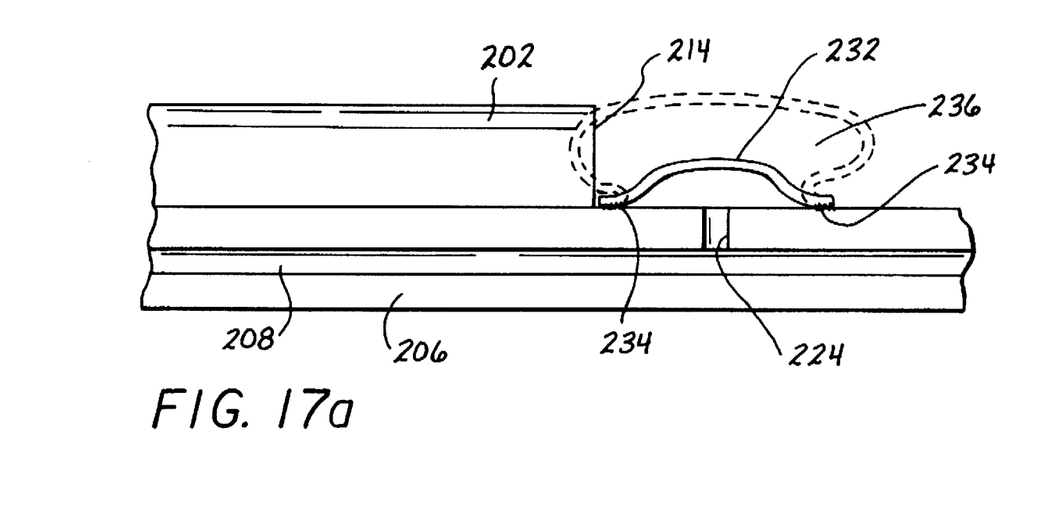
FIG. 17a is side plan view of FIG. 16c with an alternative embodiment of the balloon.
Figure 17B:
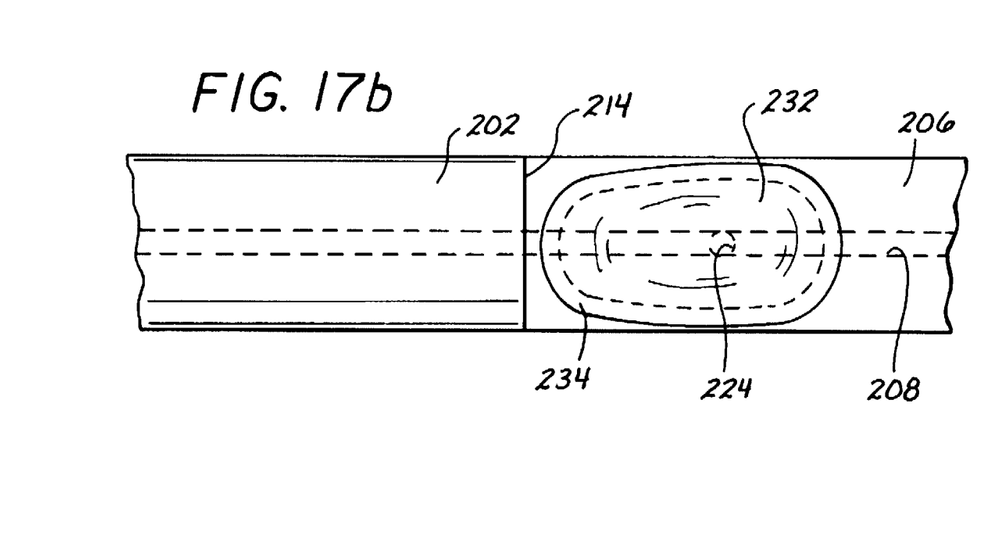

Another embodiment of the invention is shown in the side elevational view of FIG. 17a which is the identical partial side view of FIG. 16c, but wherein balloon 218, which is formed into the shape of a teardrop in the case of FIGS. 16a–d, is replaced instead by an oval balloon 232 as best depicted in the top plan view of FIG. 17b. In the embodiment of FIGS. 17a and 17b, balloon 232 is peripherally bonded in an oval outline to septum wall 206 extended from orifice 214 along a circumferential bonding area 234. Bond 234 may be bonded either in the form of a folded underbond with ends extending into the interior 236 of balloon 232 in a manner similar to bonded area 226 of balloon 218, or may be folded flatly or the bond not folded over as in the form of bond 228 of balloon 218 in FIG. 16c. In the preferred embodiment, bond 234 is not folded over and the inflated balloon 232 expands, and folds or billows over bond 234 as it moves toward, fills and seals tip orifice 214.

Figure 18A:
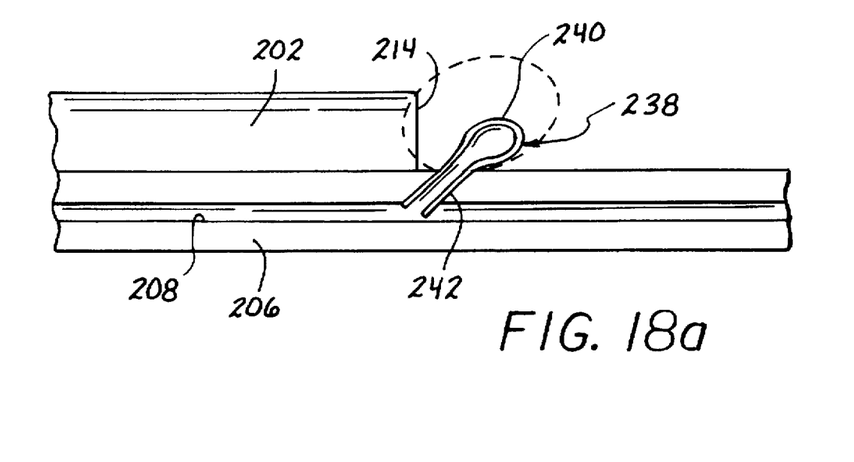
FIG. 18a is side plan view of FIG. 16c with another alternative embodiment of the balloon.
Figure 18B:
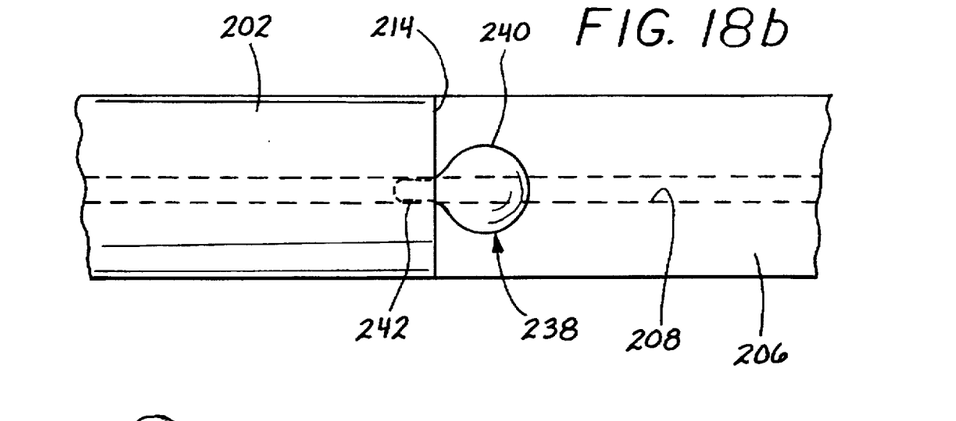

Another embodiment to the invention is shown in enlarged side elevational view in FIG. 18a and in top elevational view in FIG. 18b in a manner similar to FIGS. 16c and 16d and FIGS. 17a and 17b. In the embodiment of FIGS. 18a and 18b, balloon 238 is fabricated more in the form of a spherical conventional toy balloon with an expansible spherical member 240 in a balloon neck 242 which extends into lumen 208. Balloon 238 is then expanded to form a generally spherical envelope as shown in dotted outline in FIG. 18a to enter and seal tip orifice 214.

Tip orifice 214 as shown in the cross-sectional view of FIG. 16b is a portion of a half circle and cross section. Therefore, the tendency of balloon 240 to form a spherical shape must be deformed, at least of that portion which expands and extends into tip orifice 214, to assume a more conforming half-circle envelope. It may be possible that small portions, such as a corner of the cross section, may not be completely filled by balloon 238 and the possibility of some leakage may occur. The effects of this leakage is minimized by filling lumens 210 and 212 with an anticlotting fluid which will substantially equalize the pressure gradient across the balloon seal or provide a very small positive or negative pressure within the lumen 210 or 212 so that such leakage as may occur is in a predetermined direction. The cross sectional configurations of the embodiments of FIGS. 16a–d and 17a and 17b have a more flattened bottom profile nearly matching, or in fact, completely matching the hemispherical profile of tip orifice 214.

Figure 19:
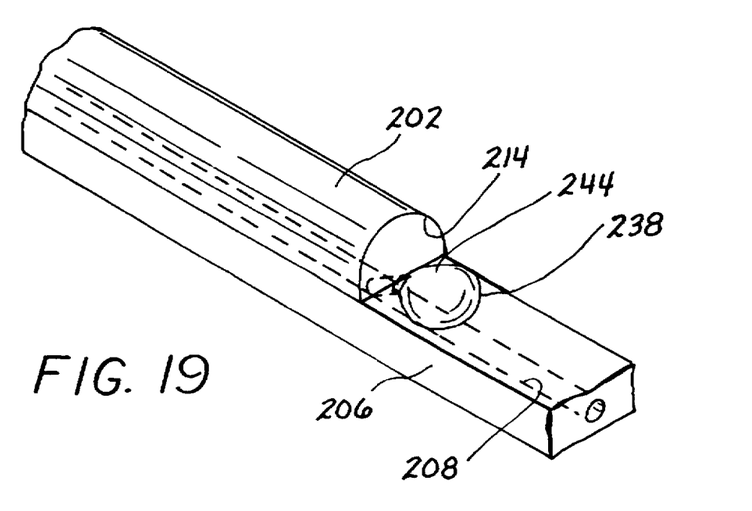
FIG. 19 is a perspective view of another embodiment of the balloon valve of FIGS. 18a and b.

Alternatively, as shown in the perspective view of FIG. 19 a balloon may be used to move a soft sealing valve flap 244 integrally formed as part of wall 206 which as a conforming shape to more precisely fit and seal orifice 214. In this case, balloon 238 does not provide the sealing, but is an actuator to move sealing flap 244. Flap 244 can also be shaped to provide to coact with balloon 238 to seal just the corners of orifice 214 that balloon 238 cannot adequately seal.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the essential idea of the invention.

We claim:

1. A permanent endovascular catheter adapted for providing a fluid comprising:
    a catheter body defining a lumen for providing the flow of said fluid through said catheter body;
    a membrane valve disposed exterior to said lumen and coupled to said catheter body; and
    at least one orifice defined in said catheter body through which said fluid within said lumen communicates exteriorly to said catheter body, said membrane valve being located at a position adjacent to said orifice and being inflatable so that by virtue of said position of said membrane valve it substantially seals said orifice by inflation of said membrane valve at said position,
    whereby said permanent catheter is subject to minimal risk of occlusion by bodily fluids.

2. The catheter of claim 1 where said orifice is a tip orifice of said catheter.

3. The catheter of claim 1 wherein said membrane valve has an uninflated and inflated configuration and is disposed in said uninflated configuration entirely exterior to said lumen so that reduction of flow through said lumen and clot formation in said lumen, caused by said membrane valve when uninflated, is substantially avoided.

4. The catheter of claim 3 wherein said membrane valve is expansible at least in part by folding of said membrane when in said uninflated configuration.

5. The catheter of claim 1 further comprising a plurality of lumens, a corresponding plurality of membrane valves each of which are disposed exterior to said plurality of lumens, a plurality of tip orifices defined in said catheter body through which fluid within said lumen may communicate exteriorly to said catheter body being closable by said corresponding plurality of membrane valves, said membrane valves being inflatable to at least partially occlude said corresponding tip orifice to selectively close said corresponding tip orifices to prevent communication therethrough exterior to said catheter body.

6. The catheter of claim 5 wherein at least two of said plurality of said membrane valves are inflated in parallel.

7. The catheter of claim 1 wherein said lumen is free of all other occluding elements which might impede flow of fluid therethrough other than said membrane valve.

8. The catheter of claim 1 wherein said lumen is closed solely by said membrane valve without coaction with any other element within said lumen.

9. The catheter of claim 1 wherein said orifice is a tip orifice and said valve membrane is affixed to said catheter adjacent to said orifice and is formed to inflate in the shape of at least a portion of a tear drop having a blunt end disposed toward tip orifice.

10. The catheter of claim 9 where said blunt end of said valve membrane has a peripheral edge which is folded under and bonded to said catheter.

11. The catheter of claim 1 wherein said orifice is a tip orifice, wherein said valve membrane is affixed to said catheter adjacent to said orifice and is formed to inflate in the shape of at least a portion of an oval having a narrowed end disposed toward tip orifice.

12. The catheter of claim 1 wherein said orifice is a tip orifice, wherein said valve membrane is affixed to said catheter adjacent to said orifice and is formed to inflate in the shape of at least a portion of a sphere.

13. A permanent endovascular catheter comprising:
    a catheter body defining a lumen within said body;
    a membrane valve disposed exterior to said lumen;
    at least one orifice defined in said catheter body through which fluid within said lumen may communicate exteriorly to said catheter body said membrane valve being inflatable to at least partially obstruct flow therethrough: and
    a moveable valve flap rotatably coupled to said catheter adjacent to said orifice, and wherein said membrane valve comprises an inflatable balloon and said flap is actuated by said balloon to substantially seal said orifices
    whereby said permanent catheter is subject to minimal risk of occlusion by bodily fluids.

14. A permanent endovascular catheter comprising:
    a catheter body defining a lumen within said body:
    a membrane valve disposed exterior to said lumen;
    at least one orifice defined in said catheter body through which fluid within said lumen may communicate exteriorly to said catheter body, said membrane valve being inflatable to at least partially obstruct flow therethrough; and
    a guide disposed on said catheter adjacent to said orifice, and wherein said membrane valve comprises an inflatable balloon whose inflation is guided by said guide to substantially seal said orifice,
    whereby said permanent catheter is subject to minimal risk of occlusion by bodily fluids.

15. A permanent endovascular catheter comprising:
    a catheter body defining a lumen within said body;
    a membrane valve disposed exterior to said lumen; and
    at least one orifice defined in said catheter body through which fluid within said lumen may communicate exteriorly to said catheter body, said membrane valve being inflatable to at least partially obstruct flow therethrough;

wherein said catheter body further comprises a septum wall, said septum wall dividing said catheter body into a plurality of longitudinal lumens, each said lumen having at least one said orifice defined in said catheter body to communicate each of said longitudinal lumens exterior to said catheter body, said catheter further comprising a corresponding plurality of membrane valves disposed on said septum wall, each of said plurality of membrane valves being disposed exterior to said corresponding orifice, whereby said permanent catheter is subject to minimal risk of occlusion by bodily fluids.

16. The catheter of claim 15 wherein at least two of said plurality of said membrane valves are serially inflated.

17. A permanent endovascular catheter comprising:

a catheter body defining a lumen within said body;

a membrane valve disposed exterior to said lumen; and at least one orifice defined in said catheter body through which fluid within said lumen may communicate exteriorly to said catheter body, said membrane valve being inflatable to at least partially obstruct flow therethrough;

wherein said orifice is a tip orifice, wherein said valve membrane is affixed to said catheter adjacent to said orifice and is formed to inflate in the shape of at least a portion of an oval having a narrowed end disposed toward tip orifice, and where said oval shaped valve membrane has peripheral edges and is not folded under along its peripheral edges where it is bonded to said catheter, whereby said permanent catheter is subject to minimal risk of occlusion by bodily fluids.

18. A method for selectively sealing a lumen defined within an endovascular catheter, said lumen having an orifice and an extending wall adjacent but exterior to said orifice of said lumen comprising:

providing an expansible membrane on said extending wall adjacent but exterior to said orifice of said lumen; and selectively expanding said expansible membrane to substantially seal said orifice only by said expansion of said expansible membrane, whereby said catheter may be used as a permanent indwelling catheter.

\* \* \* \* \*